United States Patent
Komori et al.

(10) Patent No.: US 6,307,045 B1
(45) Date of Patent: Oct. 23, 2001

(54) PROCESS FOR PRODUCING HALOGENATED BENZENE COMPOUND

(75) Inventors: Hiroshi Komori, Kawanishi (JP); Kazuhiko Nishioka, Greenwich, CT (US)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/608,217

(22) Filed: Jun. 30, 2000

(30) Foreign Application Priority Data

Jul. 5, 1999 (JP) .................................. 11-190306

(51) Int. Cl.⁷ .................. C07B 39/00; C07B 59/00; C07C 205/12; C07C 41/22; C07D 243/26
(52) U.S. Cl. .................. 540/511; 564/442; 568/937
(58) Field of Search ................. 424/1.85, 1.89; 540/511; 564/442; 568/937

(56) References Cited

U.S. PATENT DOCUMENTS

| | | | |
|---|---|---|---|
| 4,450,149 | | 5/1984 | Kabalka . |
| 4,735,792 | * | 4/1988 | Srivastava ................ 424/1.1 |
| 4,942,231 | * | 7/1990 | Mertens ................ 540/586 |
| 5,154,913 | * | 10/1992 | De Paulis et al. ................ 424/1.1 |
| 5,213,787 | * | 5/1993 | Wilbur et al. ................ 424/1.1 |
| 5,609,848 | * | 3/1997 | Wilbur et al. ................ 424/1.85 |

FOREIGN PATENT DOCUMENTS

98/18499 * 5/1998 (WO) .................. A61K/51/04

OTHER PUBLICATIONS

Adam, Michael J. et al., "Site–specific bromination of aromatic compounds: a rapid method for radiobromine labelling"; J. Chem. Soc., Chem. Commun. (1982), (11), pp. 625–626.
Seevers, Robert H. et al, Chem. Rev. 1982, 82, 575–590.
Linsebigler, Amy L. et al, Chem. Rev. 1995, 95, 735–758.
Moerlein, Stephen M. et al, J. Chem. Soc. Perkin Trans. 1 1985, pp. 1941–1947.
Fitzmaurice, Donald J. et al, J. Phys. Chem. 1993, 97, pp. 3806–3812.
Wang, Chong M. et al, J. Am. Chem. Soc. 1990, 112, pp. 2016–2018.
Guide to Radioiodination Techniques, Amersham Life Science, 1993, pp. 36–55.

* cited by examiner

*Primary Examiner*—Johann Richter
*Assistant Examiner*—Brian J. Davis
(74) *Attorney, Agent, or Firm*—Birch, Stewart, Kolasch & Birch, LLP

(57) ABSTRACT

The present invention provides a process for producing halogenated benzene compounds. In the process, an organometallic compound represented by the general formula [I]:

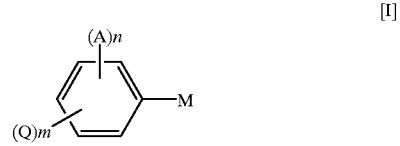

wherein M represents an $R^1_3Sn$ group, an $R^1_3Si$ group, an $R^1_3Ge$ group, an $(R^2CO_2)Hg$ group, a ClHg group or an $(R^3O)_2B$ group wherein each $R^1$ independently represents a $C_1$–$C_8$ alkyl group, $R^2$ represents a $C_1$–$C_3$ alkyl group or a $C_1$–$C_3$ haloalkyl group, $R^3$ represents a hydrogen atom or a $C_1$–$C_3$ alkyl group, n represents an integer of from 0 to 4, m represents an integer of from 0 to 1, each A independently represents a fluorine atom, a nitro group, a cyano group, a $C_1$–$C_8$ alkyl group, a $C_1$–$C_8$ alkoxy group or a $C_2$–$C_8$ acyloxy group, and Q represents an organic residue, is reacted in a solvent with a halide ion represented by the general formula $X^-$, under light irradiation conditions in the presence of a semiconductor catalyst with a photocatalytic activity.

5 Claims, No Drawings

PROCESS FOR PRODUCING HALOGENATED BENZENE COMPOUND

BACKGROUND OF THE INVENTION

1. Field of the Invention

The present invention relates to a process for producing a halogenated benzene compound, the process comprising the step of reacting in a solvent an organometallic compound with a halide ion ($X^-$), under light irradiation conditions in the presence of a semiconductor catalyst with a photocatalytic activity, particularly to a process useful for producing a halogenated benzene compound labeled with a radioactive halogen.

2. Description of the Related Art

Halogenated benzene compounds have an important role as various biologically active substances typified by drugs and agrochemicals and as intermediates for their synthesis. Further, compounds including a radioactive halogen in their molecules have extremely valuable as a radioactive tracer which is used for elucidating in-vivo behavior of drugs and the like in the course of their development, or as in-vivo or in-vitro diagnostic or therapeutic drugs for clinical diagnosis or therapy. Among the compounds including a radioactive halogen in their molecules to be used for these purposes, N-isopropylamphetamine hydrochloride labeled with iodine-123 is used as an in-vivo diagnostic drug for brain functions, 15-(p-iodophenyl)-3-(R,S)-methylpentadecanoic acid is used as that for heart diseases, and an iodohippuric acid sodium salt is used as that for kidney and urinary tract diseases, for example.

In recent years, a labeling method utilizing the exchange of a metal such as tin, silicon and germanium with a halogen has been widely used as a technique for producing such compounds including a radioactive halogen in their molecules because products with high specific radioactivities can be obtained in high position selectivities. However, since raw materials to be used for labeling are generally available with stability in the form of halide ions, the above method requires complicated operations, for example, of conducting the reaction in the presence of an oxidizing agent (sometimes, in large excess) such as hypochlorite, chloramine T (N-chloro-4-methylbenzenesulfonamide sodium salt), Iodo-Gen™ (1,3,4,6-tetrachloro-3α,6α-diphenylglycoluril), Iodo-beads™ (N-chloro-benzenesulfonamide (sodium salt) derivatized, uniform, nonporous, polystyrene beads), hydrogen peroxide and NBS (1-Bromosuccinimide), and of removing the remaining oxidizing agent by, for example, adding a reducing agent at the completion of the reaction.

Further, in the above method, the compound to be labeled is exposed to oxidizing conditions. Therefore, it is difficult to apply the method when the compound to be labeled is unstable in such conditions.

SUMMARY OF THE INVENTION

The object of the present invention is to provide a widely-applicable process for producing halogenated compounds, the process being useful for the production of compounds possessing a halogen, particularly a radioactive halogen, in their molecules.

Under such circumstances, the present inventors have studied intensively, and have found a process for producing a halogenated benzene compound represented by the general formula [II]:

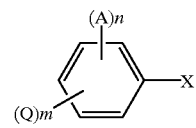

[II]

wherein X, n, m, A and Q have the same meanings as those defined below, the process comprising the step of reacting in a solvent an organometallic compound represented by the general formula [I]:

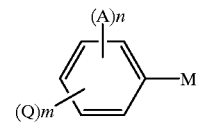

[I]

wherein M represents an $R^1_3Sn$ group, an $R^1_3Si$ group, an $R^1_3Ge$ group, an $(R^2CO_2)Hg$ group, a ClHg group or an $(R^3O)_2B$ group wherein each $R^1$ independently represents a C1–C8 alkyl group, $R^2$ represents a C1–C3 alkyl group or a C1–C3 haloalkyl group, $R_3$ represents a hydrogen atom or a C1–C3 alkyl group, n represents an integer of from 0 to 4, m represents an integer of from 0 to 1, each A independently represents a fluorine atom, a nitro group, a cyano group, a C1–C8 alkyl group, a C1–C8 alkoxy group or a C2–C8 acyloxy group, and Q represents an organic residue, with a halide ion represented by the general formula X– wherein X represents a halogen atom including each isotope thereof, under light irradiation conditions in the presence of a semiconductor catalyst with a photocatalytic activity (hereinafter, the process is referred to as the process of the present invention).

In the process of the present invention, the reaction can be conducted under mild conditions without the whole reaction system being exposed to oxidative conditions. Since the process uses the halide ion as the source of the halogen atom to be introduce, it is suitable particularly for the production of labeled compounds which should be synthesized in high purities and in high specific radioactivities from small amounts of radioactive raw materials for the halogenation which have restricted chemical forms.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step.

DETAILED DESCRIPTION OF THE INVENTION

The semiconductor catalysts with the photocatalytic activity to be used in the process of the present invention are semiconductor catalysts which are solid catalysts with the property that electrons in a valence band of the catalysts are excited by light. Most of the catalysts are metal oxides or metal sulfides. Specific examples of them include titanium oxide ($TiO_2$), strontium titanate ($SrTiO_3$), tungsten oxide ($WO_3$), bismuth oxide ($Bi_2O_3$), zirconium oxide ($ZrO_2$), stannum oxide ($SnO_2$), zinc oxide (ZnO) and zinc sulfide (ZnS). The semiconductor catalyst with the photocatalytic activity may have any form as long as its solid surface can receive light during its use. For example, powder, granule and ones supported on carriers by coating are available. Further, commercially available ones may also be employed.

The amount, in molar ratio, of the semiconductor catalyst is preferably not less than that of the halide ion ($X^-$). When the concentration of the halide ion in a solution is low, the amount of the semiconductor catalyst is preferably excessive.

The light to be used in the process of the present invention may be any one which has a wavelength at which the light can excite electrons of the semiconductor catalyst. For example, when titanium oxide ($TiO_2$), strontium titanate ($SrTiO_3$) or tungsten oxide ($WO_3$) is used, any light with wavelengths shorter than 388 nm may be applied. A black light, a mercury lamp, a xenon lamp and the like can be employed as a light source.

Examples of the halide ion ($X^-$) to be used in the process of the present invention include an iodide ion ($I^-$), a bromide ion ($Br^-$) and a chloride ion ($Cl^-$). The halide ion is used in the form of its salt of a metal such as an alkali metal or of a quaternary ammonium such as tetrabutylammonium. Examples of such salts include sodium iodide (NaI), potassium iodide (KI), sodium bromide (NaBr), potassium bromide (KBr), sodium chloride (NaCl) and potassium chloride (KCl). Furthermore, the halide ion also includes ions of isotopes of the halogen. The isotopes may be radioactive isotopes. Examples of such isotopes include iodines-123, 125, 128 and 131, bromines-75, 76, 77, 80 and 82, and chlorines-36 and 38.

The reaction in the process of the present invention is conducted in a solvent. The solvent to be used may be any one in which the organometallic compound [I], which is one of the raw materials, can be dissolved with stability and a small amount of a salt of a halide can be dissolved. Preferred are a multipolar-non-proton solvent such as acetonitrile, DMF or DMSO and its solvent mixed with water.

The reactor in which the reaction of the process of the present invention is conducted may be any one made of a material through which light with a desired wavelength can pass. A borosilicate glass reactor and the like may be used. The light source is mounted near the reactor and, as needed, is cooled for the purpose of prevention of temperature rise in the reactor caused by the heat from the light source. The reaction solution is stirred depending upon demand.

The organometallic compound represented by the general formula [I], which is used in the process of the present invention, may be produced by the producing process shown in scheme 1, for example.

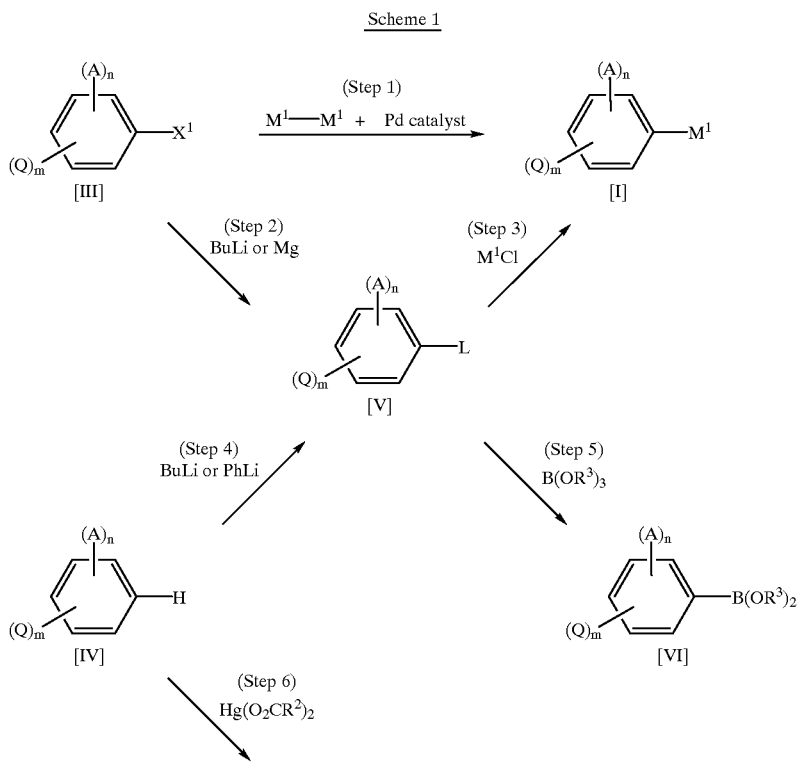

Scheme 1

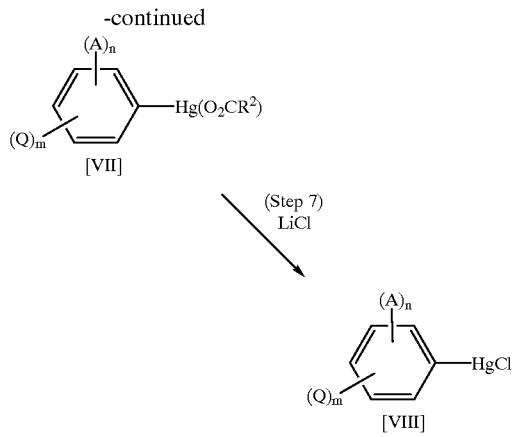

In the scheme, $X^1$ represents a chlorine atom, a bromine atom or an iodine atom, L represents Li or $MgX^1$, $M^1$ represents an $R^1_3Sn$ group, an $R^1_3Si$ group or an $R^1_3Ge$ group wherein each $R^1$ has the same meaning as that previously defined, and $R^2$, $R^3$, n, m, A and Q have the same meanings as those previously defined.

(Step 1) is carried out by reacting in a solvent the compound represented by the general formula [III] with the compound represented by the general formula $M^1$—$M^1$ (for example, $Bu_3Sn$—$SnBu_3$ and $Me_3Si$—$SiMe_3$) in a solvent in the presence of a palladium catalyst (for example, $PdCl_2$ and $(Ph_3P)_4Pd$).

(Step 2) is carried out by reacting in a solvent the compound represented by the general formula [III] with BuLi or Mg.

(Step 3) is carried out by reacting in a solvent the compound represented by the general formula [V] with the compound represented by the general formula $M^1Cl$ (for example, $BU_3SnCl$, $Me_3SiCl$ and $Me_3GeCl$).

(Step 4) is carried out by reacting in a solvent the compound represented by the general formula [IV], preferably having a substituent such as an alkoxy group at the ortho position of the reactive site, with BuLi or PhLi.

(Step 5) is carried out by reacting in a solvent the compound represented by the general formula [V] with the compound represented by the general formula $B(OR^3)_3$ (for example, $B(OCH_3)_3$).

(Step 6) is carried out by reacting in a solvent the compound represented by the general formula [IV] with the compound represented by the general formula $Hg(O_2CR^2)_2$ (for example, $Hg(O_2CCH_3)_2$ and $Hg(O_2CCF_3)_2$).

(Step 7) is carried out by reacting in a solvent the compound represented by the general formula [VII] with LiCl.

The organometallic compound represented by the general formula [I] may also be produced by constructing the moiety of the A group or the Q group after constructing the moiety of the M group.

M in the general formula [I] represents an $R^1_3Sn$ group, an $R^1_3Si$ group, an $R^1_3Ge$ group, an $(R^2CO_2)Hg$ group, a ClHg group or an $(R^3O)_2B$ group. Examples of the $R^1_3Sn$ group include a $Me_3Sn$ group, an $Et_3Sn$ group, a $Pr_3Sn$ group and a $Bu_3Sn$ group. Examples of the $R^1_3Si$ group include a $Me_3Si$ group. Examples of the $R^1_3Ge$ group include a $Me_3Ge$ group. Examples of the $(R^2CO_2)Hg$ group include a $CH_3CO_2Hg$ group and a $CF_3CO_2Hg$ group. Examples of the $(R^3O)_2B$ group include a $(MeO)_2B$ group and a $(HO)_2B$ group.

Each A in the general formula [I] independently represents a fluorine atom, a nitro group, a cyano group, a C1–C8 alkyl group, a C1–C8 alkoxy group or a C2–C8 acyloxy group. Examples of the C1–C8 alkyl group include a Me group, an Et group and a Pr group. Examples of the C1–C8 alkoxy group include a MeO group, an EtO group and a PrO group. Examples of the C2–C8 acyloxy group include an acetoxy group and a propionyloxy group.

Q in the general formula [I] represents an organic residue. Examples of the organic residue include alkyl groups which may be optionally substituted such as a 2-(N,N-dimethylamino)ethyl group, a 2-(N-isopropylamino)propyl group and a 13-methyl-14-carboxyltetradecyl group, alkanoyl groups which may be optionally substituted, a carboxyl group, alkoxycarbonyl groups which may be optionally substituted, carbamoyl groups which may be optionally substituted such as an N-(carboxymethyl) carbamoyl group, alkoxy groups which may be optionally substituted such as a carboxymethoxy group, alkanoyloxy groups which may be optionally substituted, alkoxycarbonyloxy groups which may be optionally substituted, carbamoyloxy groups which may be optionally substituted, alkylamino groups which may be optionally substituted, alkanoylamino groups which may be optionally substituted, cyclic hydrocarbon groups (, such as cyclopropyl groups, cyclohexyl groups, phenyl groups, anthryl groups or phenanthryl groups,) which may be optionally substituted, heterocyclic groups which may be optionally substituted such as a benzo(f) 1H-1,4-diazepin-5-yl group. In the above explanation, examples of the optionally substituting group may include alkyl groups or halogen atoms.

In this specification, Me represents a methyl group, Et represents an ethyl group, Pr represents a propyl group and Bu represents a butyl group.

The reaction in the process of the present invention may also be conducted further in the presence of an electron acceptor other than the raw materials. Preferable electron acceptors are ions of metals whose ionization tendencies are greater than that of a hydrogen atom. In particular, when titanium oxide ($TiO_2$), strontium titanate ($SrTiO_3$), tungsten oxide ($WO_3$), bismuth oxide ($Bi_2O_3$), zirconium oxide ($ZrO_2$) or stannum oxide ($SnO_2$) is used as the semiconductor catalyst with the photocatalytic activity, a silver ion ($Ag^+$) is preferred. Concretely, the silver ion is used as salts such as silver sulfate ($Ag_2SO_4$). The metal ion as the electron acceptor is preferably used in an amount, in molar ratio, as much as twice or more that of the halide ion ($X^-$).

The reaction in the process of the present invention may be stopped only by quitting the light irradiation. The reaction rate also may be easily controlled by selecting the quantity of light. The wavelength also may be selected. After the completion of the reaction, the desired halogenated benzene compound may be obtained by subjecting the reaction solution to column chromatography or HPLC after, if necessary, separating (for example, filtering off) the semiconductor catalyst with a photocatalytic activity.

According to the process of the present invention, halogenated benzene compounds can be produced under mild conditions. The present invention process is useful particularly in the field of the production of labeled compounds which should be synthesized in high purities and in high specific radioactivities from small amounts of radioactive raw materials for the halogenation which have restricted chemical forms.

EXAMPLES

The present invention will be concretely explained with reference to examples. The invention, however, is not limited to the examples.

Although there is no clear statement in the examples, light sources were installed at positions about 10 to 30 cm above the reactors.

The qualitative and quantitative analysis of the target compounds were conducted based on the retention time measuring method and the areametric analysis by means of high performance liquid chromatography for the desired halogenated benzene compounds (commercially available products or products produced by other methods).

Example 1

Into a borosilicate glass vessel (a 5-ml sample tube manufactured by Maruemu), a solution of tri-n-butyl(4-nitrophenyl) stannane (8.01 mg, 19.4 µmol) in acetonitrile (1.0 ml) was placed and then titanium oxide ($TiO_2$, manufactured by Sakai Chemical Industry Co., Ltd.) (0.12 mg, 1.50 µmol), silver sulfate (0.23 mg, 738 nmol, manufactured by Wako Pure Chemical Industries Ltd.), sodium iodide (474 ng, 3.16 nmol, 3-µL aqueous solution, manufactured by Wako Pure Chemical Industries Ltd.) and [$^{125}$I] sodium iodide (6.14 MBq, 0.08 nmol 2-µL aqueous solution, manufactured by Amersham) were added and a lid was put on the vessel. Under static conditions, the system was irradiated for 20 minutes at room temperature with a xenon lamp (2 KW, manufactured by Ushio Inc.) obliquely from the upper side. After stopping the irradiation, water was added to the reaction solution, and the mixture was extracted with benzene. The extracted organic layer was analyzed by means of radio high performance liquid chromatography. The radiochemical purity of 4-[$^{125}$I]iodonitrobenene was not lower than 98% and the yield thereof was 85% on the basis of the amount of the [$^{125}$I] sodium iodide used.

Radio high performance chromatography analysis conditions:
　Column: SUMIPAX ODS A-212, 6 mm ID×15 cm, 5 µm, a reverse phase mode high performance (or pressure) liquid chromatography column packed with octadecyl ($C_{18}$) silylated silica gel, manufactured by Sumika Chemical Analysis Service;
　Mobile phase: acetonitrile/water=1/1 volume/volume;
　Flow rate: 1.0 ml/minute
　Detector: Radioactivity detector;
　4-[$^{125}$I]iodonitrobenzene retention time: 16.6 minutes.

Example 2

Into a borosilicate glass vessel (a 5-ml sample tube manufactured by Maruemu), a solution of tri-n-butyl(4-methoxyphenyl) stannane (7.62 mg, 19.2 µmol) in acetonitrile (1.0 ml) was placed and then a grain of glass bead coated with titanium oxide ($TiO_2$) (manufactured by Kato Manufacturing Co., Inc.), silver sulfate (4.90 µg, 15.7 nmol, 9.1-µL aqueous solution, manufactured by Wako Pure Chemical Industries Ltd.), sodium iodide (474 ng, 3.16 nmol, 3-µL aqueous solution, manufactured by Wako Pure Chemical Industries Ltd.) and [$^{125}$I] sodium iodide (2.30 MBq, 0.03 nmol, 1-µL aqueous solution, manufactured by Amersham) were added and a lid was put on the vessel. Under static conditions, the system was irradiated for 210 minutes at room temperature with a black light (5 W, manufactured by NEC Corp.). After stopping the irradiation, water was added to the reaction solution, and the mixture was extracted with benzene. The organic layer extracted was analyzed by means of radio high performance liquid chromatography. The radiochemical purity of 4-[$^{125}$I]iodoanisole was not lower than 98% and the yield thereof was 69% on the basis of the amount of the [$^{125}$I] sodium iodide used.

Radio high performance chromatography analysis conditions:
　Column: SUMIPAX ODS A-212. 6 mm ID×15 cm, 5 µm, a reverse phase mode high performance (or pressure) liquid chromatography column packed with octadecyl ($C_{18}$) silylated silica gel, manufactured by Sumika Chemical Analysis Service;
　Mobile phase: acetonitrile/water=1/1 volume/volume;
　Flow rate: 1.0 ml/minute
　Detector: Radioactivity detector;
　4-[$^{125}$I]iodoanisole retention time: 23.6 minutes.

Example 3

Into a borosilicate glass vessel (a 5-ml sample tube manufactured by Maruemu), a solution of 7-chloro-1-methyl-5-(2'-fluoro-4'-tri-n-butylstannyl)phenyl-3H-1,4-benzodiazepin-2(1H)-one (1.44 mg, 2.43 µmol) in acetonitrile (1.0 ml) was placed and then titanium oxide ($TiO_2$, manufactured by Sakai Chemical Industry Co., Ltd.) (0.13 mg, 1.63 µmol), silver sulfate (0.25 mg, 802 nmol, manufactured by Wako Pure Chemical Industries Ltd.), sodium iodide (474 ng, 3.16 nmol, 3-µL aqueous solution, manufactured by Wako Pure Chemical Industries Ltd.) and [$^{125}$I] sodium iodide (6.00 MBq, 0.08 nmol, 2-µL aqueous solution, manufactured by Amersham) were added and a lid was put on the vessel. Under static conditions, the system was irradiated for 20 minutes at room temperature with a xenon lamp (2 KW, manufactured by Ushio Inc.) obliquely from the upper side. After stopping the irradiation, the reaction solution was filtered, and the filtrate was analyzed by means of radio high performance liquid chromatography. The radiochemical purity of 7-chloro-1-methyl-5-(2'-fluoro-4'-[$^{125}$I]iodo)phenyl-3H-1,4-benzodiazepin-2(1H)-one was 84% and the yield thereof was 89% on the basis of the amount of the [$^{1251}$] sodium iodide used.

Radio high performance chromatography analysis conditions:
　Column: SUMIPAX ODS A-212, 6 mm ID×15 cm, 5 µm, a reverse phase mode high performance (or pressure) liquid chromatography column packed with octadecyl ($C_{18}$) silylated silica gel, manufactured by Sumika Chemical Analysis Service;
　Mobile phase: acetonitrile/water=1/1 volume/volume;
　Flow rate: 1.0 ml/minute
　Detector: Radioactivity detector;
　7-chloro-1-methyl-5-(2'-fluoro-4'-[$^{125}$I]iodo)phenyl-3H-1,4-benzodiazepin-2(1H)-one retention time: 28.6 minutes.

Example 4

Into a borosilicate glass vessel (a 5-ml sample tube manufactured by Maruemu), a solution of tri-n-butyl(4-nitrophenyl) stannane (7.98 mg, 19.4 μmol) in acetonitrile (0.5 ml) was placed and then strontium titanate ($StTiO_3$, manufactured by Wako Pure Chemical Industries Ltd.) (0.21 mg, 1.14 μmol), silver sulfate (0.18 mg, 577 nmol, manufactured by Wako Pure Chemical Industries Ltd.), sodium iodide (468 ng, 3.12 nmol, 3-μL aqueous solution, manufactured by Wako Pure Chemical Industries Ltd.) and [$^{125}$I] sodium iodide (1.08 MBq, 0.014 nmol, 1-μL aqueous solution, manufactured by Amersham) were added and a lid was put on the vessel. Under static conditions, the system was irradiated for 5 hours at room temperature with a black light (5 W, manufactured by NEC Corp.) obliquely from the upper side. After stopping the irradiation, the supernatant of the reaction solution was analyzed by means of radio high performance liquid chromatography. The radiochemical purity of 4-[$^{125}$I]iodonitrobenzene was 88%.

Radio high performance chromatography analysis conditions:

Column: SUMIPAX ODS A-212, 6 mm ID×15 cm, 5 μm, a reverse phase mode high performance (or pressure) liquid chromatography column packed with octadecyl ($C_{18}$) silylated silica gel, manufactured by Sumika Chemical Analysis Service;

Mobile phase: acetonitrile/water=1/1 volume/volume;

Flow rate: 1.0 ml/minute

Detector: Radioactivity detector;

4-[$^{125}$I]iodonitrobenzene retention time: 17.5 minutes;

[$^{125}$I]iodide ion retention time: 2.1 minutes.

Example 5

Into a borosilicate glass vessel (a 5-ml sample tube manufactured by Maruemu), a solution of tri-n-butyl(4-nitrophenyl) stannane (10.4 mg, 25.2 μmol) in acetonitrile (1.0 ml) was placed and then tungsten oxide ($WO_3$, manufactured by Wako Pure Chemical Industries Ltd.) (0.52 mg, 2.24 μmol), silver sulfate (0.31 mg, 994 nmol, manufactured by Wako Pure Chemical Industries Ltd.), sodium iodide (468 ng, 3.12 nmol, 3-μL aqueous solution, manufactured by Wako Pure Chemical Industries Ltd.) and [$^{125}$I] sodium iodide (1.45 MBq, 0.019 nmol, 1-μL aqueous solution, manufactured by Amersham) were added and a lid was put on the vessel. Under static conditions, the system was irradiated for 160 minutes at room temperature with a black light (5 W, manufactured by NEC Corp.) obliquely from the upper side. After stopping the irradiation, the supernatant of the reaction solution was analyzed by means of radio high performance liquid chromatography. The radiochemical purity of 4-[$^{125}$I]iodonitrobenene was 84%.

Radio high performance chromatography analysis conditions:

Column: SUMIPAX ODS A-212, 6 mm ID×15 cm, 5 μm, a reverse phase mode high performance (or pressure) liquid chromatography column packed with octadecyl ($C_{18}$) silylated silica gel, manufactured by Sumika Chemical Analysis Service;

Mobile phase: acetonitrile/water=1/1 volume/volume;

Flow rate: 1.0 ml/minute

Detector: Radioactivity detector;

4-[$^{125}$I]iodonitrobenzene retention time: 17.0 minutes;

[$^{125}$I]iodide ion retention time: 2.2 minutes.

Example 6

Into a borosilicate glass vessel (a 5-ml sample tube manufactured by Maruemu), a solution of tri-n-butyl(4-nitrophenyl) stannane (8.47 mg, 20.6 μmol) in acetonitrile (0.5 ml) was placed and then bismuth oxide ($Bi_2O_3$) (0.58 mg, 1.24 μmol, manufactured by Wako Pure Chemical Industries Ltd.), silver sulfate (0.19 mg, 609 nmol, manufactured by Wako Pure Chemical Industries Ltd.), sodium iodide (468 ng, 3.12 nmol, 3-μL aqueous solution, manufactured by Wako Pure Chemical Industries Ltd.) and [$^{125}$I] sodium iodide (1.08 MBq, 0.014 nmol, 1-μL aqueous solution, manufactured by Amersham) were added and a lid was put on the vessel. Under static conditions, the system was irradiated for 5 hours at room temperature with a black light (5 W, manufactured by NEC Corp.) obliquely from the upper side. After stopping the irradiation, the supernatant of the reaction solution was analyzed by means of radio high performance liquid chromatography. The radiochemical purity of 4-[$^{125}$I]iodonitrobenene was 97%.

Radio high performance chromatography analysis conditions:

Column: SUMIPAX ODS A-212, 6 mm ID×15 cm, 5 μm, a reverse phase mode high performance (or pressure) liquid chromatograph column packed with octadecyl ($C_{18}$) silylated silica gel, manufactured by Sumika Chemical Analysis Service;

Mobile phase: acetonitrile/water=1/1 volume/volume;

Flow rate: 1.0 ml/minute

Detector: Radioactivity detector;

4-[$^{125}$I]iodonitrobenzene retention time: 17.5 minutes;

[$^{125}$I]iodide ion retention time: 2.2 minutes.

Example 7

Into a 1-L borosilicate glass beaker, a solution of tri-n-butyl(4-nitrophenyl) stannane (98.4 mg, 239 μmol) in acetonitrile (100 ml) was placed and then titanium oxide ($TiO_2$, manufactured by Sakai Chemical Industry Co., Ltd.) (20.3 mg, 254 μmol), silver sulfate (40.1 mg, 129 μmol, manufactured by Wako Pure Chemical Industries Ltd.) and sodium iodide (36.3 mg, 242 μmol, manufactured by Wako Pure Chemical Industries Ltd.) were added. Then, the opening of the beaker was covered with a colorless transparent film of polyvinyl chloride. Under static conditions, the system was irradiated for 50 hours at room temperature with a xenon lamp (2 KW, manufactured by Ushio Inc.) obliquely from the upper side. After stopping the irradiation, the supernatant of the reaction solution was analyzed by means of UV high performance liquid chromatography. The yield of 4-iodonitrobenzene on the basis of the amount of the sodium iodide used was 80%. Further, the yield of 4-iodonitrobenzene was determined with time in the reaction. The yield of the target compound increased almost in proportion to the reaction time.

UV high performance chromatography analysis conditions:

Column: SUMIPAX ODS A-212, 6 mm ID×15 cm, 5 μm, a reverse phase mode high performance (or pressure) liquid chromatography column packed with octadecyl ($C_{18}$) silylated silica gel, manufactured by Sumika Chemical Analysis Service;

Mobile phase: acetonitrile/water=1/1 volume/volume;

Flow rate: 1.0 ml/minute

Detector: Ultraviolet spectroscopic detector (254 nm);

4-iodonitrobenzene retention time: 17.3 minutes.

The yield was calculated by the UV working curve method.

Example 8

Into a borosilicate glass vessel (a 5-ml sample tube manufactured by Maruemu), a solution of tri-n-butyl(4- nitrophenyl) stannane (9.26 mg, 22.5 μmol) in acetonitrile (1.0 ml) was placed and then titanium oxide TiO$_2$, manufactured by Sakai Chemical Industry Co., Ltd.) (0.22 mg, 2.75 μmol), silver sulfate (0.46 mg, 1.48 μmol, manufactured by Wako Pure Chemical Industries Ltd.) and sodium bromide (2.10 μg, 20.4 nmol, 2-μL aqueous solution, manufactured by Wako Pure Chemical Industries Ltd.) were added and a lid was put on the vessel. Under static conditions, the system was irradiated for 8 hours at room temperature with a black light (5 W, manufactured by NEC Corp.) obliquely from the upper side. After stopping the irradiation, the supernatant of the reaction solution was analyzed by means of UV high performance liquid chromatography. The yield of 4-bromonitrobenzene on the basis of the amount of the sodium bromide used was 65%.

UV high performance chromatography analysis conditions:

Column: SUMIPAX ODS A-212, 6 mm ID×15 cm, 5 μm, a reverse phase mode high performance (or pressure) liquid chromatography column packed with octadecyl (C$_{18}$) silylated silica gel, manufactured by Sumika Chemical Analysis Service;

Mobile phase: acetonitrile/water=1/1 volume/volume;

Flow rate: 1.0 ml/minute

Detector: Ultraviolet spectroscopic detector (254 nm);

4-bromonitrobenzene retention time: 14.6 minutes.

The yield was calculated by the UV working curve method.

Next, a process for producing the organometallic compound represented by the general formula [I] which is used in the process of the present invention is described as a Referential Example.

Referential Example (Production of tri-n-butyl(4-nitrophenyl)stannane)

To a 4-bromonitrobenzene (606 mg, 3.00 mmol, manufactured by Tokyo Kasei) solution in toluene (5 ml), bis(tributyltin) (3480 mg, 6.00 mmol, manufactured by Merck & Co., Inc.) and tetrakis(triphenylphosphine)palladium(0) (45.0 mg, 39.0 μmol, manufactured by Kanto Chemical Co., Ltd.) were added and the mixture was refluxed for 2 hours at a bath temperature of 120° C. The reaction mixture was then cooled to room temperature and filtered. The residue was washed with ether. The filtrate was washed with water and a saturated brine in sequence, and then the solvent was removed by distillation under reduced pressure. The residue was subjected to column chromatography (silica gel, hexane) to yield tri-n-butyl(4-nitrophenyl)stannane (570 mg, 1.38 mmol) in a yield of 46% on the basis of the 4-bromonitrobenzene used.

What is claimed is:

1. A process for producing a halogenated benzene compound represented by the formula II:

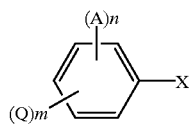

II wherein X, n, m, A and Q have the meanings defined below, the process comprising the step of reacting in a solvent a halide with an organometallic compound represented by the formula I:

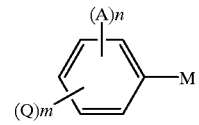

I wherein M represents an R$^1_3$Sn group, an R$^1_3$Si group, and R$^1_3$Ge group, an (R$^2$CO$_2$)Hg group, a ClHg group or an (R$^3$O)$_2$B group, wherein each R$^1$ independently represents a C$_1$–C$_8$ alkyl group, R$^2$ represents a C$_1$–C$_3$ alkyl group or a C$_1$–C$_3$ haloalkyl group, R$^3$ represents a hydrogen atom or a C$_1$–C$_3$ alkyl group, n represents an integer of from 0 to 4, m represents an integer of from 0 to 1, each A independently represents a fluorine atom, a nitro group, a cyano group, a C$_1$–C$_8$ alkyl group, a C$_1$–C$_8$ alkoxy group or a C$_2$–C$_8$ acyloxy group, and Q represents an optionally substituted alkyl group, an optionally substituted alkanoyl group, a carboxyl group, an optionally substituted alkoxycarbonyl group, an optionally substituted carbamoyl group, an optionally substituted alkoxy group, an optionally substituted alkanoyloxy group, an optionally substituted alkoxycarbonyloxy group, an optionally substituted carbamoyloxy group, an optionally substituted alkylamino group, an optionally substituted alkanoylamino group, an optionally substituted cyclic hydrocarbon group, and an optionally substituted heterocyclic group;

with said halide ion represented by the formula X$^-$ wherein X represents a halogen atom including each isotope thereof, said reaction occurring in the presence of a semiconductor catalyst having photocatalytic activity and light having a wavelength which can excite electrons of said catalyst.

2. The process according to claim 1, wherein the halide ion is a halide ion being a radioisotope.

3. The process according to claim 1, wherein the halide ion is an iodide ion (I$^-$), a bromide ion (Br$^-$) or a chloride ion (Cl$^-$).

4. The process according to claim 1, wherein the semiconductor catalyst with a photocatalytic activity is at least one kind selected from the group consisting of titanium oxide (TiO$_2$), strontium titanate (SrTiO$_3$), tungsten oxide (WO$_3$), bismuth oxide (Bi$_2$O$_3$), zirconium oxide (ZrO$_2$), stannum oxide (SnO$_2$), zinc oxide (ZnO) and zinc sulfide (ZnS).

5. The process according to claim 1, wherein the reaction is carried out further in the presence of a silver ion.

* * * * *